(12) United States Patent
Hasmann et al.

(10) Patent No.: US 9,687,568 B2
(45) Date of Patent: *Jun. 27, 2017

(54) COMPOSITION OF A FIRST NON-LABELED MONOCLONAL ANTIBODY BINDING TO A TUMOR ANTIGEN AND A NON-CROSS REACTIVE SECOND MONOCLONAL ANTIBODY LABELED WITH A NIR FLUORESCENCE LABEL

(71) Applicant: Hoffmann-La Roche Inc., Nutley, NJ (US)

(72) Inventors: Max Hasmann, Munich (DE); Helmut Lenz, Tutzing (DE); Werner Scheuer, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 182 days.

This patent is subject to a terminal disclaimer.

(21) Appl. No.: 13/961,167

(22) Filed: Aug. 7, 2013

(65) Prior Publication Data

US 2013/0323180 A1   Dec. 5, 2013

Related U.S. Application Data

(63) Continuation of application No. 12/599,713, filed as application No. PCT/EP2008/004456 on Jun. 4, 2008, now Pat. No. 8,529,901.

(30) Foreign Application Priority Data

Jun. 6, 2007  (EP) ..................... 07011087

(51) Int. Cl.
*A61K 49/00* (2006.01)
*A61K 39/395* (2006.01)

(52) U.S. Cl.
CPC .... *A61K 49/0058* (2013.01); *A61K 39/39558* (2013.01); *A61K 49/0032* (2013.01)

(58) Field of Classification Search
CPC ............ A61K 49/0017; A61K 49/0019; A61K 49/0021; A61K 49/0032; A61K 49/0058; A61K 49/16; A61K 39/395; A61K 39/39558
See application file for complete search history.

(56) References Cited

U.S. PATENT DOCUMENTS 4,921,690 A   5/1990 Beatty et al.
6,096,289 A   8/2000 Goldenberg

FOREIGN PATENT DOCUMENTS

WO   WO 2006/082515 A2   8/2006

OTHER PUBLICATIONS

Hilger, I., et al., Eur. Radiol., 14: 1124-1129, 2004.*
Ke, S., et al. Cancer Research 63: 7870-7875, 2003.*
Ballou et al., 1997, "Tumor detection and visualization using cyanine fluorochrome-labeled antibodies," Biotechnol. Prog. 13(5): 649-658.
Borchardt et al., 2003, "Targeted actinium-225 in vivo generators for therapy of ovarian cancer," Cancer Res. 63(16): 5084-5090.
Cai et al., 2005, "Multimodality tumor imaging targeting integrin alphavbeta3," Biotechniques 39 (6 Suppl): S14-S25.
Hilger et al., 2004, "Near-infrared fluorescence imaging of HER-2 protein over-expression in tumour cell," Eur. Radiol. 14(6): 1124-1129.
Nahta et al., 2007, "Trastuzumab: triumphs and tribulations," Oncogene 26(25): 3637-3643.
Persson et al., 2005, "[(177)Lu]pertuzumab: experimental studies on targeting of HER-2 positive tumour cells," Eur. J. Nucl. Med. Mol. Imaging 32(12): 1457-1462.
Ramjiawan et al., 2000, "Noninvasive localization of tumors by immunofluorescence imaging using a single chain Fv fragment of a human monoclonal antibody with broad cancer specificity," Cancer 89(5): 1134-1144.
Robinson et al., 2005, "Quantitative immuno-positron emission tomography imaging of HER2-positive tumor xenografts with an iodine-124 labeled anti-HER2 diabody," Cancer Res. 65(4): 1471-1478.
Rosenthal et al., 2006, "In vivo detection of head and neck cancer orthotopic xenografts by immunofluorescence," Laryngoscope 116(9): 1636-1641.
Sachdev et al., 2006, "Inhibitors of insulin-like growth factor signaling: a therapeutic approach for breast cancer," J. Mammary Gland Biol. Neoplasia. 11(1): 27-39.
Shi et al., 2003, "Near-infared optical imaging of epidermal growth factor receptor in breast cancer xenografts," Cancer Res. 63(22): 7870-7875.
Soukos et al., 2001, "Epidermal Growth Factor receptor-targeted immunophotodiagnosis and photoimmunotherapy of oral precancer in vivo," Cancer Res. 61(11): 4490-4496.
Spies, 2004, "Imaging and dosing in radioimmunotherapy with Yttrium 90 ibritumomab tiuxetan (Zevalin)," Semin. Nucl. Med. 34(1 Suppl. 1): 10-13.
Sridhar et al., 2003, "Inhibitors of epidermal-growth-factor receptors: a review of clinical research with a focus on non-small-cell lung cancer," Lancet Oncol. 4(7):397-406.
Tang et al., 2005, "Imaging of HER2/neu expression in BT-474 human breast cancer xenografts in athymic mice using [(99m)TC]-HYNIC-trastuzumab (Herceptin) Fab fragments," Nucl. Med. Commun. 26(5): 427-432.

(Continued)

*Primary Examiner* — Anne Holleran
(74) *Attorney, Agent, or Firm* — Jones Day

(57) ABSTRACT

This invention relates to a composition of a non-labeled monoclonal antibody binding to a tumor antigen and a second monoclonal antibody labeled with a NIR fluorescence label, binding to the same tumor antigen, wherein the first and second antibody exhibit no cross reactivity. The composition can be used for the treatment of patients suffering of solid tumors which are associated with an overexpression of such a tumor antigen. The invention further relates to a the co-administration of said first and second antibody as wells as to a method of acquiring a NIR fluorescence images of such tumors or the patients suffering from such tumors during the treatment of said patient with such composition.

23 Claims, 6 Drawing Sheets

(56) References Cited

OTHER PUBLICATIONS

Ramjiawan, et al, 2000, "Noninvasive localization of tumors by immunofluorescence imaging using a single chain Fv fragment of a human monoclonal antibody with broad cancer specificity," Cancer, American Cancer Society, Philadelphia PA 89(5): 1134-1144.

* cited by examiner

COMPOSITION OF A FIRST NON-LABELED MONOCLONAL ANTIBODY BINDING TO A TUMOR ANTIGEN AND A NON-CROSS REACTIVE SECOND MONOCLONAL ANTIBODY LABELED WITH A NIR FLUORESCENCE LABEL

This invention relates to a composition of a non-labeled monoclonal antibody binding to a tumor antigen and a second monoclonal antibody labeled with a NIR fluorescence label, binding to the same tumor antigen, wherein the first and second antibody exhibit no cross reactivity. The composition can be used for the treatment of patients suffering of solid tumors which are associated with an overexpression of such a tumor antigen. The invention further relates to the co-administration of said first and second antibody as well as to a method of acquiring a NIR fluorescence images of such tumors or the patients suffering from such tumors during the treatment with such composition or the co-administration of such antibodies.

BACKGROUND OF THE INVENTION

Monoclonal Antibodies in the Therapy

In an ongoing quest to improve the therapeutic arsenal against cancer, a fourth weapon other than surgery, chemotherapy and radiotherapy has emerged, i.e. targeted therapy. Targeted therapy includes tyrosine kinase receptor inhibitors (small molecule inhibitors like imatinib, gefitinib, and erlotinib), proteasome inhibitors (bortezomib), biological response modifiers (denileukin diftitox) and monoclonal antibodies (MAbs). The remarkable specificity of MAbs as targeted therapy makes them promising agents for human therapy. Not only can MAbs be used therapeutically to protect against disease, they can also be used to diagnose a variety of illnesses, measure serum protein and drug levels, type tissue and blood and identify infectious agents and specific cells involved in immune response. About a quarter of all biotech drugs in development are MAbs, and about 30 products are in use or being investigated. A majority of the MAbs are used for the treatment of cancer. (Gupta, N.; et al., Indian Journal of Pharmacology 38 (2006) 390-396; Funaro, A.; et al., Biotechnology Advances 18 (2000) 385-401; Suemitsu, N. et al., Immunology Frontier 9 (1999) 231-236) Labeled Monoclonal Antibodies and In-Vivo Imaging Several in vivo imaging methods are available for the quantification of therapeutic antibodies in tumor tissue usually based on labeled derivatives of the antibodies. Said labeled antibodies usually include antibodies labeled with radiolabels such as, e.g. $^{124}$I, $^{111}$In, $^{64}$Cu, and others, for use in positron emission tomography (PET) (see e.g. Robinson, M. K., et al., Cancer Res 65 (2005) 1471-1478; Lawrentschuk, N., et al., BJU International 97 (2006) 916-922; Olafsen, T., et al., Cancer Research 65 (2005) 5907-5916; and Trotter, D. E., et al., Journal of Nuclear Medicine 45 (2004) 1237-1244), $^{123}$I, $^{125}$I, and $^{99m}$Tc and others for use in single photon emission computed tomography (SPECT) (see e.g. Orlova, A., et al., Journal of Nuclear Medicine 47 (2006) 512-519; Dietlein, M., et al., European Journal of Haematology 74 (2005) 348-352).

Also nonradioactive labels are known for in-vivo imaging techniques, e.g. near-infrared (NIR) fluorescence labels, activatable dyes, and engodogenous reporter groups (fluorescent proteins like GFP-like proteins, and bioluminescent imaging) (Licha, K., et al., Adv Drug Deliv Rev, 57 (2005) 1087-1108). Especially NIR fluorescence imaging can be used for the quantification of therapeutic antibodies in tumor tissue. Advantages of near infrared imaging over other currently used clinical imaging techniques include the following: potential for simultaneous use of multiple, distinguishable probes (important in molecular imaging); high temporal resolution (important in functional imaging); high spatial resolution (important in vivo microscopy); and safety (no ionizing radiation).

There exist different monoclonal antibodies covalently coupled to a NIR fluorescence label (Hilger, I., et al, Eur Radial (2004) 1124-1129; Ballou, B., et al., Cancer Immunol Immunother. 41 (4) (1995) 257-63; Ballou, B., et al., Proceedings of SPIE—The International Society for Optical Engineering 2680 (1996) 124-131; Ballou, B., et al., Biotechnol Prog. (1997) 649-58; Ballou, B., et al., Cancer detection and prevention (1998), 22 251-257 Becker, A., et al., Nature Biotechnology 19 (2001) 127-131; Montet, X., et al., Cancer Research 65 (2005), 6330-6336; Rosenthal, E. L., et al., The Laryngoscope 116 (2006) 1636-1641; EP 1619501, WO 2006/072580, WO 2004/065491 and WO 2001/023005) which were used as single agents for NIR fluorescence imaging.

In NIR fluorescence imaging, filtered light or a laser with a defined bandwidth is used as a source of excitation light. The excitation light travels through body tissues. When it encounters a near infrared fluorescent molecule ("contrast agent"), the excitation light is absorbed.

The fluorescent molecule then emits light (fluorescence) spectrally distinguishable (slightly longer wavelength) from the excitation light. Despite good penetration of biological tissues by near infrared light, conventional near infrared fluorescence probes are subject to many of the same limitations encountered with other contrast agents, including low target/background ratios.

Near infrared wavelengths (approximately 640-1300 nm) have been used in optical imaging of internal tissues, because near infrared radiation exhibits tissue penetration of up to 6-8 centimeters. See, e.g., Wyatt, J. S., and Kirkpatrick, P. J., Phil. Trans. R. Soc. B 352 (1997) 701-705; Tromberg, et al., Phil. Trans. R. Soc. London B 352 (1997) 661-667.

The exact amounts of the antibody-label conjugates used for in vivo imaging depends on the different characteristics and aspects of the labels used, e.g. for NIR fluorescence labels the quantum yield of the label is one of the criteria for the amount of label or labeled antibody used (see e.g. WO 2006/072580).

Therapy Monitoring During Treatment with Monoclonal Antibodies

Factors affecting the successful therapy of malignant diseases include the antibody dose used and the schedule of administration, the half-life and fast blood clearance of the antibodies, the presence of circulating antigen, poor tumor penetration of the high/mol.-wt. monoclonal antibody (MAb) and the way in which these molecules are catabolized. At present, there is a lack of knowledge about many aspects of the physiological function and metabolism of antibodies. (Iznaga-Escobar, N. et al, Meth. Find. Exp. Clin. Pharm. 26(2) (2004) 123-127). Therefore it is important to monitor the course of such therapies.

The success of such treatments is usually assessed using different imaging techniques like chest X-ray, computed tomography (CT), computerized axial tomography (CAT), molecular resonance imaging (MRI), positron emission tomography (PET), single photon emission computed tomography (SPECT), fluorescence imaging (FI), and bioluminescent imaging (BLI) (see e.g. Helms, M. W, et al., Contributions to microbiology 13 (2006) 209-231 and Pantel, K., et al., JNCI 91 (1999) 1113-1124). It is often defined as a "Response" to the treatment. According to RECIST criteria tumor response for solid tumors (Therasse, et al., J. Nat. Cancer Institute. 92 (2000) 205-216) is categorized in dependency of the volume progression or regression of the tumors (e.g. measured via CT) into four levels: complete response (CR) or partial response (PR), stable disease (SD) and progressive disease (PD) (see Table 1). Furthermore the European Organization for Research and Treatment of Cancer (EORTC) proposed a categorization into four levels in dependency of the metabolism of the tumors measured via 2-[$^{18}$F]-Fluoro-2-deoxyglucose positron emission tomography (FDG-PET) (Young, H., et al., Eur J Canc 35 (1999) 1773-1782 and Kelloff, G. J., et al, Clin Canc Res 11 (2005) 2785-2808): complete metabolic response (CMR) or partial metabolic response (PMR), stable metabolic disease (SMD) and progressive metabolic disease (PMD) (see Table 2). Recently a combined assessment with CT and PET gets more and more common. While CT mainly focuses on the development of tumor size it delivers only restricted information on the tumor metabolism and is associated with exposure to radioactive radiation, PET imaging gives more insight in the tumor metabolism, but still radioactive labels are needed for this technique.

SUMMARY OF THE INVENTION

The invention comprises a pharmaceutical composition comprising
   a) a non-labeled monoclonal antibody binding to a tumor antigen and
   b) a second monoclonal antibody labeled with a NIR fluorescence label, specifically binding to the same tumor antigen,
   characterized in that, the first and second antibody exhibit no cross reactivity.

Such composition can be composed of either one compartment comprising both antibodies or of two compartments, one comprising the non-labeled monoclonal antibody and one comprising the labeled monoclonal antibody Preferably the non-labeled monoclonal antibody is an anti-HER2 antibody, preferably trastuzumab or pertuzumab.

In another preferred embodiment the non-labeled monoclonal antibody is an anti-EGFR antibody, preferably caetuximab or rhMab ICR62.

One embodiment of the invention is the use of a non-labeled monoclonal antibody specifically binding to a tumor antigen for the manufacture of a medicament for the treatment of a patient suffering from a solid tumor overexpressing said tumor antigen
wherein the non-labeled monoclonal antibody is co-administered with a second monoclonal antibody labeled with a NIR fluorescence label, specifically binding to the same tumor antigen, characterized in that the first and second antibody exhibit no cross reactivity.

Another embodiment of the invention is the use of a non-labeled monoclonal antibody specifically binding to a tumor antigen for the manufacture of a medicament for the treatment of a patient suffering from a solid tumor overexpressing said tumor antigen previously treated with said non-labeled monoclonal antibody and a second monoclonal antibody labeled with a NIR fluorescence label, specifically binding the same tumor antigen whereby after said previous treatment the fluorescence signal in a region of the solid tumor has decreased by at least 10%, preferably at least 20%, more preferably at least 30%, compared to the NIR fluorescence signal in said region of the solid tumor before said previous treatment with said non-labeled monoclonal antibody; characterized in that the first and second antibody exhibit no cross reactivity.

Another aspect of the invention is the use of a non-labeled monoclonal antibody specifically binding to a tumor antigen for the manufacture of a pharmaceutical composition for the treatment of patient suffering from a solid tumor overexpressing said tumor antigen, wherein the administration pattern of the medicament comprises the following, steps
a) the patient receives a first dose with a second monoclonal antibody labeled with a NIR fluorescence label, specifically binding to the same tumor antigen;
b) the NIR fluorescence signal of said second monoclonal antibody labeled with a NIR fluorescence label in a region of the solid tumor is measured;
c) the patient receives a first dose with said non-labeled monoclonal antibody;
d) the patient receives a second dose with said second antibody labeled with a NIR fluorescence label;
e) the NIR fluorescence signal of said second monoclonal antibody labeled with a NIR fluorescence label in said region of the solid tumor is measured and has decreased by at least 10%, preferably at least 20%, more preferably at least 30%, compared to the signal measured under b);
f) the patient receives a second dose with said non-labeled monoclonal antibody based on the result of the measurement of step e);
characterized in that the first and second antibody exhibit no cross reactivity.

Another aspect of the invention is the use of a monoclonal antibody labeled with a NIR fluorescence label, specifically binding to a tumor antigen for the manufacture of a pharmaceutical composition for the treatment of a patient suffering from a solid tumor overexpressing said tumor antigen.

Another aspect of the invention is the use of a non-labeled, monoclonal antibody specifically binding to a tumor antigen for the manufacture of a medicament for the treatment of a solid tumor wherein, during said treatment, a second monoclonal antibody labeled with a NIR fluorescence label, specifically binding to the same tumor antigen is used to monitor the treatment, characterized in that the first and second antibody exhibit no cross reactivity.

Another aspect of the invention is a method for acquiring a NIR fluorescence image of a patient suffering from a solid tumor overexpressing a tumor antigen which has received a dose of a first, non-labeled, monoclonal antibody specifically binding to said tumor antigen and a dose of a second monoclonal antibody labeled with a NIR fluorescence label specifically binding to the same tumor antigen, wherein the NIR fluorescence signal of in a region of the solid tumor is measured characterized in that the first and second antibody exhibit no cross reactivity.

Another aspect of the invention is a method for acquiring a NIR fluorescence image wherein the signal of a monoclonal antibody labeled with a NIR fluorescence label specifically binding to a tumor antigen, in a region of a solid tumor is measured during the treatment of a patient suffering from a solid tumor overexpressing a tumor antigen with a monoclonal antibody specifically binding to the same tumor antigen, characterized in that the first and second antibody exhibit no cross reactivity.

Another aspect of the invention is a method for determining NIR fluorescence signal of a monoclonal antibody labeled with a NIR fluorescence label specifically binding to a tumor antigen in a region of the solid tumor during the treatment of a patient suffering from a solid tumor overexpressing a tumor antigen with a non-labeled, monoclonal antibody specifically binding to the same tumor antigen, wherein the following steps were performed:

a) the patient receives a first dose with a second monoclonal antibody labeled with a NIR fluorescence label, specifically binding to the same tumor antigen, wherein the first and second antibody exhibit no cross reactivity, b) the NIR fluorescence signal of said second monoclonal antibody labeled with a NIR fluorescence label in a region of the solid tumor is measured, c) the patient receives a first dose with said non-labeled monoclonal antibody d) the patient receives a second dose with said second antibody labeled with a NIR fluorescence label, e) the NIR fluorescence signal of said second monoclonal antibody labeled with a NIR fluorescence label in said region of the solid tumor is measured and has decreased by at least 10%, preferably at least 20%, more preferably at least 30%, compared to the signal measured under b);

f) the patient receives a second dose with said non-labeled monoclonal antibody based on the result of the measurement of step e);

characterized in that the first and second antibody exhibit no cross reactivity.

DETAILED DESCRIPTION OF THE INVENTION

The term "antibody" encompasses the various forms of antibodies including but not being limited to whole antibodies, human antibodies, humanized antibodies and genetically engineered antibodies like monoclonal antibodies, chimeric antibodies or recombinant antibodies as well as fragments of such antibodies as long as the characteristic properties according to the invention are retained.

The terms "monoclonal antibody" or "monoclonal antibody composition" as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. Human antibodies are well-known in the state of the art (van Dijk, M. A., and van de Winkel, J. G., Curr. Opin. Pharmacol. 5 (2001) 368-374). Based on such technology, human antibodies against a great variety of targets can be produced. Examples of human antibodies are for example described in Kellermann, S. A., et al., Curr Opin Biotechnol. 13 (2002) 593-597.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, may not naturally exist within the human antibody germline repertoire in vivo.

As used herein, "specifically binding" refers to an antibody specifically binding to the tumor antigen (for which the antibody is specific). Preferably the binding affinity is of $K_D$-value of $10^{-8}$ mol/l or higher (e.g. $10^{-9}$ mol/l), preferably with a $K_D$-value of $10^{-9}$ mol/l or higher, more preferably with a $K_D$-value of $10^{-10}$ mol/l or higher. The binding affinity is determined with a standard binding assay, such as surface plasmon resonance technique (Biacore®).

The term "nucleic acid molecule", as used herein, is intended to include DNA molecules and RNA molecules. A nucleic acid molecule may be single-stranded or double-stranded, but preferably is double-stranded DNA.

The "constant domains" are not involved directly in binding the antibody to an antigen but are involved in the effector functions (ADCC, complement binding, and CDC).

The "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the O-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat, E. A., et al., Sequences of Proteins of Immunological Interest, 5th Ed. Public Health Service, National Institutes of Health, Bethesda, Md. (1991)) and/or those residues from a "hypervariable loop".

A "tumor antigen," as used herein, includes the meaning known in the art, which includes any molecule expressed on (or associated with the development of) a tumor cell that is known or thought to contribute to a tumorigenic characteristic of the tumor cell. Numerous tumor antigens are known in the art. Whether a molecule is a tumor antigen can also be determined according to techniques and assays well known to those skilled in the art, such as for example clonogenic assays, transformation assays, in vitro or in vivo tumor formation assays, gel migration assays, gene knockout analysis, etc. Preferably the term "tumor antigen" when used herein refers to a human transmembrane protein i.e., a cell membrane proteins which is anchored in the lipid bilayer of cells. The human transmembrane protein will generally comprise an "extracellular domain" as used herein, which may bind a ligand; a lipophilic transmembrane domain, a conserved intracellular domain tyrosine kinase domain, and a carboxyl-terminal signaling domain harboring several tyrosine residues which can be phosphorylated. The tumor antigen include molecules such as EGFR, HER2/neu, HER3, HER4, Ep-CAM, CEA, TRAIL, TRAIL-receptor 1, TRAIL-receptor 2, lymphotoxin-beta receptor, CCR4, CD19, CD20, CD22, CD28, CD33, CD40, CD80, CSF-1R, CTLA-4, fibroblast activation protein (FAP), hepsin, melanoma-associated chondroitin sulfate proteoglycan (MCSP), prostate-specific membrane antigen (PSMA), VEGF receptor 1, VEGF receptor 2, IGF1-R, TSLP-R, TIE-1, TIE-2, TNF-alpha, TNF like weak inducer of apoptosis (TWEAK), IL-1R, preferably EGFR, HER2/neu, CEA, CD20, or IGF1-R; more preferably HER2/neu or EGFR, still more preferably HER2/neu.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors characterized by overexpression of the tumor antigen can be determined by standard assays known in the art. Preferably overexpression is measured in fixed cells of frozen or paraffin-embedded tissue sections using immunohistochemical (IHC) detection. When coupled with histological staining, localization of the targeted protein can be determined and extent of its expression within a tumor can be measured both qualitatively and semi-quantitatively. Such IHC detection assays are known in the art and include e.g. the Clinical Trial Assay (CTA), the commercially available LabCorp 4D5 test for the HER2 antigen, and the commercially available DAKO HercepTest® (DAKO, Carpinteria, Calif.) for the HER2 tumor antigen. The latter assay uses a specific range of 0 to 3+ cell staining (0 being normal expression, 3+ indicating the strongest positive expression) to identify cancers having overexpression of the HER2 protein (see the Herceptin® (trastuzumab) full prescribing information; September 1998; Genentech, Inc., San Francisco, Calif.). Thus, e.g. with regard to the HER2 tumor antigen patients having a solid tumor characterized by overexpression of the HER2 tumor antigen in the range of 1+, 2+, or 3+, preferably 2+ or 3+, more preferably 3+ would benefit from the methods of therapy of the present invention. Alternatively such overexpression can be detected by determination of the NIR fluorescence signal in a region of the solid tumor of a monoclonal antibody labeled with a NIR fluorescence label, specifically binding to said tumor antigen and comparison of said NIR fluorescence signal or image in a region of the solid tumor to the NIR fluorescence signal or image of the non-tumorous tissue or other tumors non-overexpressing said tumor antigen (see e.g. Examples 1 and 2, FIGS. 1 and 2).

The term "the first and second antibody exhibit no cross reactivity" refers to the first non-labeled monoclonal antibody specifically binding to a tumor antigen and a second monoclonal antibody labeled with a NIR fluorescence label, specifically binding to the same tumor antigen wherein these two antibodies show no cross reactivity with respect to said tumor antigen. The cross reactivity of these two antibodies with regards to the same tumor antigen can be detected with the help of a competitive assay. For this purpose, e.g. with the help of an enzyme immunoassay, there is tested the extent to which the first antibody competes with the second antibody for the binding to an immobilized tumor antigen. For this purpose, an appropriately immobilized tumor antigen is incubated with the first antibody which conjugated for the purpose of the assay to a detectable moiety and an excess of the second antibody. Detectable moieties include direct detectable or indirect detectable systems. By detection of the bound labeling there can easily be ascertained the extent to which the antibody in question can displace the known antibody from the binding site. If there is a displacement of more than 10%, preferably of more than 20%, at the same concentration or at higher concentrations, preferably in the case of 105-fold excess of the second antibody, referred to the known antibody, then the two antibodies exhibit cross reactivity. That means that the two antibodies bind to the same or an overlapping epitope. (See non cross reactive and cross reactive examples e.g. Examples 3, 4 and 5, FIGS. 3, 4 and 5).

By the use of such a first and second antibody which exhibit no cross reactivity a clearly improved (=higher) signal/background ratio is achieved (see e.g. Example 3: 2.88=1440MFI/500MFI—Cy5 labeled pertuzumab after trastuzumab treatment—FIG. 3*b*) compared to the signal/background ratio of a first and second antibody which exhibit cross reactivity (see e.g. Example 3: 1.06=530MFI/500MFI—Cy5 labeled trastuzumab after trastuzumab treatment FIG. 3*a*). This allows a better localization of the region of tumor than with the use of cross reactive antibodies; even if less NIRF labeled antibody is given. Thus by the use of such a first and second antibody which exhibit no cross reactivity an effective t Thus in one embodiment of the invention the signal/background ratio by the use of such a first and second antibody which exhibit no cross reactivity is at least 1.5, preferably at least 2.0.

The abbreviation MFI refers to the mean NIR fluorescence (NIRF) signal intensity [arbitrary units]) NIR fluorescence signal intensity can be quantified by summing up the number and signal intensities of the pixels in the region of interest (ROI).

The term "Signal/background ratio" refers to the signal/background ratio of the respective NIR fluorescence signal (determined as MFI) in the region of interest (ROI), e.g., the region of the solid tumor and the respective NIR fluorescence background signal (determined as MFI) e.g. the signal measured in a non-tumor tissue.

In the above competitive assay the directly detectable moieties conjugated to the first antibody (for assay purposes only) include e.g. chromogens (fluorescent or luminescent groups and dyes), enzymes, NMR-active groups or metal particles, haptens, e.g. digoxigenin, are examples of detectable labels. Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g., by the labels as mentioned above. The detectable label can also be a photoactivatable cross linking group, e.g. an azido or an azirine group. Metal chelates which can be detected by electrochemoluminescence are also preferred signal-emitting groups, with particular preference being given to ruthenium chelates, e.g. a ruthenium (bispyridyl) 32+ chelate. Suitable ruthenium labeling groups are described, for example, in EP 0 580 979, WO 90/05301, WO 90/11511, and WO 92/14138.

Examples of such first and second antibody binding to the same tumor antigen which exhibit no cross reactivity are e.g. the two anti-HER2 antibodies trastuzumab and pertuzumab, or the two anti-EGFR antibodies cetuximab and rhMab ICR62. However one skilled in the art can easily generate further non-cross reactive antibodies to tumor antigen such as EGFR, HER2/neu, HER3, HER4, Ep-CAM, CEA, TRAIL, TRAIL-receptor 1, TRAIL-receptor 2, lymphotoxin-beta receptor, CCR4, CD19, CD20, CD22, CD28, CD33, CD40, CD80, CSF-1R, CTLA-4, fibroblast activation protein (FAP), hepsin, melanoma-associated chondroitin sulfate proteoglycan (MCSP), prostate-specific membrane antigen (PSMA), VEGF receptor 1, VEGF receptor 2, IGF1-R, TSLP-R, TIE-1, TIE-2, TNF-alpha, TNF like weak inducer of apoptosis (TWEAK), IL-1R, preferably EGFR, HER2/neu, CEA, CD20, or IGF1-R. For this purpose e.g. phage display techniques can be used (as described in Henderikx et al. Cancer Res. 58 (1998) 4324-4332; Huse et al. Science 246 (1989) 1275-1281 or Kang et al. PNAS 88 (1991) 11120-11123) with subsequent chimerization and/or humanization. Also immunization techniques are well known in the art, thus immunization with the relevant tumor antigen (e.g. their DNA, the protein or fragments thereof) can be used to generate such antibodies. E.g. human antibodies to IGF-1R can be prepared according to the following procedure:

Generation of a Hybridoma Cell Line Producing Anti-IGF-IR Antibodies

Culture of Hybridomas

Generated HuMab hybridomas are cultured in Hybridoma Express Medium (PAA Laboratories GmbH, Austria) supplemented with 2 mM L-glutamine (BioWhittaker) and 4% Origen Cloning Factor (Igen, France) at 37° C. and 5% $CO_2$; or in Iscoves Modified Dulbeco's Medium (500 ml: BioWhittaker Europe, Belgium) supplemented with Fetal Clone Serum (50 ml: Hyclone, Utah), and Origen Hybridoma Cloning Factor (30 ml: Igen, Gaithersburg Md.) at 37° C. and 5% $CO_2$.

Immunization Procedure of Transgenic Mice

Ten HCo7 transgenic mice (4 males and 6 females), strain GG2201 (Medarex, San José, Calif., USA) are alternatingly immunized with $1\times10^6$ NIH 3T3 cells, transfected with an expression vector for IGF-IR, and 20 µg soluble extracellular domain of IGF-IR. Six immunizations were performed in total, three intraperitoneal (IP) immunizations with the IGF-IR expressing cells and three subcutaneous (SC) immunizations at the tail base with the recombinant protein. For the first immunization, 100 µl of $1\times10^6$ NIH 3T3 IGF-IR cells is mixed with 100 µl complete Freunds' adjuvant (CFA; Difco Laboratories, Detroit, USA). For all other immunizations, 100 µl of cells in PBS were used or recombinant protein is mixed with 100 µl incomplete Freunds' adjuvant (ICFA; Difco).

Antigen Specific ELISA

Anti-IGF-IR titers in sera of immunized mice are determined by antigen specific ELISA. IGF-IR soluble extracellular domain at a concentration of 1 µg/ml in PBS was coated overnight at 4° C., or for two hours at 37° C., to 96 wells plates. Thereafter, the wells were blocked with PBSTC (PBS supplemented with 0.05% Tween®-20 and 2% chicken serum (Gibco BRL)) for 1 hour (h) at room temperature. First tap sera were diluted 1/50 in PBSTC, sera from all other taps are pre-diluted 1/100 in PBSTC and serially diluted up to 1/6400. Diluted sera are added to the wells and incubated for 1 h at 37° C. Pre-tap serum is used as negative control. 200 ng/ml goat anti-human IGF-IR (100 µg/ml) was used as positive control. Subsequently, plates are washed twice with PBST and incubated with horse radish peroxidase (HRP)-conjugated rat anti-human IgG F(ab')$_2$ (DAKO), diluted 1/2000 in PBSTC for 1 h at 37° C. Wells are washed twice with PBST and assays were developed with freshly prepared ABTS® solution (1 mg/ml) (ABTS: 2,2'-azino bis(3-ethylbenzthiazoline-6-sulfonic acid) for 30 minutes at room temperature (RT) in the dark. Absorbance is measured at 405 nm.

FACS Analysis

In addition to determination by antigen specific ELISA, anti-IGF-IR titers in sera of immunized mice are also determined by FACS analyses. NIH 3T3 IGF-IR cells and the parental NIH 3T3 cells are incubated with diluted sera for 30 minutes at 4° C. Alternating IP and SC immunizations were performed at two weeks intervals starting with an IP immunization. Pre-tap serum (parental NIH 3T3 cells) was used as negative control. Initially, 200 ng/ml goat anti-human IGF-IR was used as positive control. Cells are washed three times in PBS supplemented with 1% bovine serum albumin and 0.01% azide. Subsequently, cells are incubated with fluorescein isothiocyanate (FITC)-conjugated antigen binding fragments (F(ab')$_2$ fragments) of rat anti-human human IgG diluted 1/100 in FACS buffer, for 30 minutes at 4° C. Cells are washed twice in FACS buffer and samples were analyzed on a FACSCalibur (Becton Dickinson, Erembodegem-Aalst, Belgium).

Boosting of Mice

When serum titers of anti-IGF-IR are found to be sufficient, mice are additionally boosted twice with 15 µg IGF-IR extracellular domain in 200 µl PBS intravenously (i.v.) 4 and 3 days before fusion.

Hybridoma Generation

Mice are sacrificed and the spleen and lymph nodes flanking the abdominal aorta and vena cava were collected. Fusion of splenocytes and lymph node cells with the fusion partner SP 2.0 cells are performed according to standard operating procedures.

κ-ELISA

To determine whether hybridomas that resulted from the fusion generate human antibodies, a κ-ELISA is performed. ELISA plates are coated with rat anti-human IgG κ-light chain antibody (DAKO) diluted 1/10000 in PBS by overnight incubation at 4° C. After discarding the wells, plates are blocked by incubation with PBSTC for 1 hour at room temperature. Thereafter, wells are incubated with hybridoma culture supernatant, ½ diluted in PBSTC. Culture medium ½ diluted in PBSTC is used as negative control, κ-light positive mouse serum 1/100 diluted in PBSTC served as positive control. Subsequently, wells are washed thrice and were incubated with HRP-conjugated rat anti-human IgG F(ab')$_2$ (DAKO), diluted 1/2000 in PBSTC for 1 h at 37° C. Wells are washed thrice and assays are developed with freshly prepared ABTS® solution (1 mg/ml) for 30 minutes at room temperature (RT) in the dark. Absorbance are measured at 405 nm in an ELISA plate reader.

In this way anti-IGF-1R antibody libraries can be generated.

All antibodies in such libraries (either generated by this technique or by another immunization or phage display technique) can afterwords be tested e.g. with the help of an enzyme immunoassay (see the general definition above and also the example of an IGF-1R Antigen specific ELISA above), whether they exhibit cross reactivity towards the same tumor antigen or not. In such a way one skilled in the art can easily generate pairs of a first and a second antibody specifically binding to the same tumor antigen which exhibit no cross reactivity.

For example using this immunization technique in this way it lays in the ordinary skills of an artisan to generate a second non-crossreactive antibody specifically binding to the same tumor antigen as a first non-labeled antibody selected from the group consisting of: alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab. Such second non-crossreactive antibody can then be labeled with a NIRF label (e.g.Cy5) and used in one of the embodiments of the invention.

The term "tumor" as used herein refer to or describe the physiological condition in mammals that is typically characterized by unregulated cell growth. Examples of tumors include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, and melanoma.

The term "solid tumors" when used herein refers to tumors selected from the group of gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer, preferably breast cancer.

The term "region of a solid tumor" when used herein refers to a zone comprising the solid tumor. The region of a solid tumor can comprise either the whole solid tumor or only regional parts of it. The NIR fluorescence signal in the region of said solid tumor is measured, and the corresponding the NIR fluorescence images are acquired in either two-dimensional or three-dimensional form, e.g. in comparison with the surrounding non-tumorous tissue or in comparison with NIR fluorescence signals or images at different time points as a reference.

The terms "co-administration", "co-administered" or "co-administering", when used herein, mean that the labeled monoclonal antibody is administered with the non-labeled monoclonal antibody. The administration of the labeled antibody with the non-labeled antibody can be carried out either as one single formulation or as two separate formulations (one for the non-labeled antibody and one for the labeled antibody). The co-administration can be simultaneous or sequential in either order, wherein preferably there is a time period while both monoclonal antibodies are simultaneously binding to the same tumor antigen on the solid tumor, as long as the tumor is still existent and as long as the tumor overexpresses said tumor antigen. If one single formulation is used, the two antibodies are co-administered simultaneously. If two separate formulations (one for the non-labeled antibody and one for the labeled antibody) are used, the two antibodies are co-administered either simultaneously (e.g. through one single continuous infusion or through two separate continuous infusions at the same time) or sequentially. When both antibodies are co-administered sequentially the labeled antibody can be administered before or after the non-labeled antibody either on the same day in two separate administrations, or e.g. the labeled antibody is administered on day 1 for acquiring a NIR fluorescence image and the non-labeled antibody is co-administered afterward e.g. on day 2 to day 7. Then after a certain period e.g. from one to 5 weeks, which may include further administration of the non-labeled antibody, the antibody labeled with a NIR fluorescence label is administered again for acquiring a NIR fluorescence image. Based on the comparison of these NIR fluorescence images which are preferably acquired in the region of the solid tumor using the same conditions (e.g. same amount of labeled antibody, same time point after administration, same acquisition time, etc.), a further administration of the non-labeled antibody will be given when the NIR fluorescence signal has decreased at least 10%, preferably at least 20% and more preferably at least 30%. The term "dose" when used herein refers to the administration of the monoclonal antibodies. The "dose" of the non-labeled monoclonal antibodies, can be e.g. in the range from about 0.05 mg/kg to about 10 mg/kg body weight. Thus, one or more consecutive doses of about 0.5 mg/kg, 2.0 mg/kg, 4.0 mg/kg or 10 mg/kg body weight may be administered to the patient. Such doses may be administered intermittently, e.g. every week or every two or three weeks, (e.g. such that the patient receives from about two to about twenty, e.g. about six doses of trastuzumab and pertuzumab each). Also, an initial higher loading dose, followed by one or more lower doses may be administered. The monoclonal antibody labeled with a NIR fluorescence label in is hereby co-administered in an amount or dose of at least 0.001 mg/kg body weight, preferably at least 0.01 mg/kg body weight, more preferably at least 0.01 mg/kg body weight. The exact amount or "dose" can vary and depends e.g. on the label and his quantum yield. The amount or "dose" of the non-labeled monoclonal antibody and the monoclonal antibody labeled with a NIR fluorescence label can be defined by the skilled artisan by simple routine experiments.

The term "administration pattern of the medicament" when used herein refers to the preferably sequential steps during administration of said medicament, which may include the administrations itself, measurement of NIR fluorescence signals in the region of the solid tumor, comparison of different NIR fluorescence signals in the region of the same solid tumor measured under the same conditions e.g. before and after administration of the non-labeled monoclonal antibody, administration of a further doses of the non-labeled monoclonal antibody base on the finding that the NIR fluorescence signals in the region of the same solid tumor has decreased during the treatment.

The term "during said treatment" with a first non-labeled monoclonal antibody when used herein refers to the co-administration of second monoclonal antibody labeled with a NIR fluorescence label which can be simultaneous or sequential in either order, wherein preferably there is a time period while both monoclonal antibodies are simultaneously binding to the same tumor antigen on the solid tumor, as long as the tumor is still existent and as long as the tumor expresses or overexpresses said tumor antigen. In connection with the term "during said treatment" with a first non-labeled monoclonal antibody the treatment period of said first non-labeled monoclonal antibody starts at the first dose administration, (and can include several consecutive administrations of said first antibody, while there is always an amount (preferably a therapeutically effective amount) of said antibody present in the patient) and ends at the time when after the last administration of said first antibody said first antibody was fully degraded within said patient (preferably when said first antibody was degraded until an residual amount which below the therapeutically effective amount).

The term "patient suffering from a solid tumor overexpressing said tumor antigen previously treated with said non-labeled monoclonal antibody" when used herein means that said at least one dose of said non-labeled monoclonal antibody has been administered to said patient before the treatment of the patient with both monoclonal antibodies.

It is self-evident that the non-labeled antibody administered to the patient in a therapeutically effective amount which is the amount of the subject compound or combination that will elicit the biological or medical response of a tissue, system, animal or human that is being sought by the researcher, veterinarian, medical doctor or other clinician.

As used herein, the term "patient" preferably refers to a human in need of treatment to treat cancer, or a precancerous condition or lesion. However, the term "patient" can also refer to non-human animals, preferably mammals such as dogs, cats, horses, cows, pigs, sheep and non-human primates, among others, that are in need of treatment.

The terms "antibody labeled with a NIR fluorescence label", "labeled antibody" or "labeled monoclonal antibody" as used herein refer to monoclonal antibodies which are conjugated to NIR fluorescence label. Conjugation techniques have significantly matured during the past years and an excellent overview is given in Aslam, M., and Dent, A., Bioconjugation, London (1998) 216-363, and in the chapter "Macromolecule conjugation" in Tijssen, P. "Practice and theory of enzyme immunoassays" (1990) 221-278 Elsevier, Amsterdam.

The term "non-labeled antibody" as used herein refers to a monoclonal antibody which is not labeled to a NIR fluorescence label nor conjugated to another moiety.

The term "NIR" as used herein means near-infrared.

The invention comprises a pharmaceutical composition comprising
  a) a non-labeled monoclonal antibody specifically binding to a tumor antigen and
  b) a second monoclonal antibody labeled with a NIR fluorescence label, specifically binding to the same tumor antigen,
  characterized in that, the first and second antibody exhibit no cross reactivity.

Such composition can be composed of either one compartment comprising both antibodies in on single formulation or of two compartments, one comprising the non-labeled monoclonal antibody in a first formulation and one comprising the labeled monoclonal antibody in a second formulation. Such composition is intended for the co-administration of such non-labeled monoclonal antibody and labeled monoclonal antibody.

In one embodiment, said tumor antigen is selected from the group consisting of EGFR, HER2/neu, HER3, HER4, Ep-CAM, CEA, TRAIL, TRAIL-receptor 1, TRAIL-receptor 2, lymphotoxin-beta receptor, CCR4, CD19, CD20, CD22, CD28, CD33, CD40, CD80, CSF-1R, CTLA-4, fibroblast activation protein (FAP), hepsin, melanoma-associated chondroitin sulfate proteoglycan (MCSP), prostate-specific membrane antigen (PSMA), VEGF receptor 1, VEGF receptor 2, IGF1-R, TSLP-R, TIE-1, TIE-2, TNF-alpha, TNF like weak inducer of apoptosis (TWEAK), IL-1R, preferably EGFR, HER2/neu, CEA, CD20, or IGF1-R; more preferably HER2/neu or EGFR, still more preferably HER2/neu.

In another embodiment, the non-labeled monoclonal antibody is an anti-HER2 antibody, preferably trastuzumab or pertuzumab, more preferably trastuzumab.

In another embodiment, the non-labeled monoclonal antibody is an anti-EGFR antibody, preferably cetuximab, rhMab ICR62, nimotuzumab, or matuzumab, more preferably cetuximab or rhMab ICR62.

In another embodiment, the non-labeled monoclonal antibody is an anti-IGF 1R antibody.

In another embodiment, the non-labeled monoclonal antibody is selected from the group of:
alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, preferably trastuzumab, cetuximab, rhMab ICR62 and pertuzumab, more preferably trastuzumab.

The composition typically comprises the antibody labeled with a NIR fluorescence label in an amount of at least 0.001 mg/kg body weight, preferably at least 0.01 mg/kg body weight, more preferably at least 0.01 mg/kg body weight. The exact amount can vary and depends e.g. on the label and his quantum yield. The amount can be defined by the skilled artisan by simple routine experiments.

Trastuzumab (sold under the trade name Herceptin®) is a recombinant humanized anti-HER2 monoclonal antibody used for the treatment of HER2 over-expressed/HER2 gene amplified metastatic breast cancer. Trastuzumab binds specifically to the same epitope of HER2 as the murine anti-HER2 antibody 4D5 described in Hudziak, R. M., et al., Mol. Cell. Biol. 9 (1989) 1165-1172. Trastuzumab is a recombinant humanized version of the murine anti-HER2 antibody 4D5, referred to as rhuMAb 4D5 or trastuzumab) and has been clinically active in patients with HER2-overexpressing metastatic breast cancers that had received extensive prior anticancer therapy. (Baselga, J., et al, J. Clin. Oncol. 14 (1996) 737-744). Trastuzumab and its method of preparation are described in U.S. Pat. No. 5,821,337.

Pertuzumab (Omnitarg®) is another recombinant humanized anti-HER2 monoclonal antibody used for the treatment of HER2 positive cancers. Pertuzumab binds specifically to the 2C4 epitope, a different epitope on the extracellular domain of HER2 as trastuzumab. Pertuzumab is the first in a new class of HER dimerisation inhibitors (HDIs). Through its binding to the HER2 extracellular domain, pertuzumab blocks ligand-activated heterodimerisation of HER2 with other HER family members, thereby inhibiting downstream signalling pathways and cellular processes associated with tumor growth and progression (Franklin, M. C., et al. Cancer Cell 5 (2004) 317-328 and Friess, T, et al. Clin Cancer Res 11 (2005) 5300-5309). Pertuzumab is a recombinant humanized version of the murine anti-HER2 antibody 2C4 (referred to as rhuMAb 2C4 or pertuzumab) and it is described together with the respective method of preparation in WO 01/00245 and WO 2006/007398.

Trastuzumab and pertuzumab are examples of first and second monoclonal antibodies specifically binding to the same tumor antigen, characterized in that, the first and second antibody exhibit no cross reactivity. Further examples include the two anti-EGFR antibodies, cetuximab and rhMab ICR62.

Cetuximab is chimeric monoclonal anti-EGFR antibody 225 (c MAb 225, U.S. Pat. No. 4,943,533 and EP 0359 282), for use in the treatment of EGFR expressing tumors. The C225 antibody (Cetuximab) was demonstrated to inhibit EGF-mediated tumor cell cascade.

The rhMab ICR62, another anti-EGFR antibody, is an recombinant humanized version of the rat ICR62 antibody and is described in WO 2006/082515.

The two anti-EGFR antibodies, cetuximab and rhMab ICR62 represent further examples of first and second monoclonal antibodies specifically binding to the same tumor antigen, characterized in that, the first and second antibody exhibit no cross reactivity.

Another aspect of the invention is the use of a non-labeled monoclonal antibody specifically binding to a tumor antigen for the manufacture of a medicament for the treatment of a patient suffering from a solid tumor overexpressing said tumor antigen
wherein the non-labeled monoclonal antibody is co-administered with a second monoclonal antibody labeled with a NIR fluorescence label, specifically binding to the same tumor antigen, characterized in that the first and second antibody exhibit no cross reactivity.

In one aspect of the invention the use of a non-labeled monoclonal antibody specifically binding to a tumor antigen for the manufacture of a medicament for the treatment of a patient suffering from a solid tumor overexpressing said tumor antigen is characterized in that a NIR fluorescence image of said patient is acquired.

In another aspect of the invention such use is characterized in that the NIR fluorescence signal of said second monoclonal antibody labeled with a NIR fluorescence label, specifically binding to the same tumor antigen in a region of the solid tumor is measured.

Another aspect of the invention is the use of a non-labeled monoclonal antibody specifically binding to a tumor antigen for the manufacture of a medicament for the treatment of a patient suffering from a solid tumor overexpressing said tumor antigen previously treated with said non-labeled monoclonal antibody and a second monoclonal antibody labeled with a NIR fluorescence label, specifically binding the same tumor antigen whereby after said previous treatment the NIR fluorescence signal in a region of the solid tumor has decreased by at least 10%, preferably at least 20%, more preferably at least 30%, compared to the NIR fluorescence signal in said region of the solid tumor before said previous treatment with said non-labeled monoclonal antibody;
characterized in that the first and second antibody exhibit no cross reactivity.

Another aspect of the invention is the use of a non-labeled monoclonal antibody specifically binding a tumor antigen for the manufacture of a medicament for the treatment of a patient suffering from a solid tumor overexpressing said tumor antigen wherein the administration pattern of the medicament comprises the following steps:
a) the patient receives a first dose with said non-labeled monoclonal antibody;
b) the NIR fluorescence signal of a second antibody labeled with a NIR fluorescence label, specifically binding to the same tumor antigen, after said first dose with said non-labeled monoclonal antibody has decreased by at least 10%, preferably at least 20%, more preferably at least 30%, in a region of the solid tumor, compared to the NIR fluorescence signal in said region of the solid tumor, before said first dose with said non-labeled monoclonal antibody;
c) the patient receives a second dose with said non-labeled monoclonal antibody based on the result of the measurement of step b);
characterized in that the first and second antibody exhibit no cross reactivity.

Preferably the steps a) to c) are carried out as consecutive steps a), b), and c).

Another aspect of the invention is the use of a non-labeled monoclonal antibody specifically binding to a tumor antigen for the manufacture of a medicament for the treatment of patient suffering from a solid tumor overexpressing said tumor antigen, wherein the administration pattern of the medicament comprises the following steps:
a) the patient receives a first dose with a second monoclonal antibody labeled with a NIR fluorescence label, specifically binding to the same tumor antigen;
b) the NIR fluorescence signal of said second monoclonal antibody labeled with a NIR fluorescence label in a region of the solid tumor is measured;
c) the patient receives a first dose with said non-labeled monoclonal antibody;
d) the patient receives a second dose with said second antibody labeled with a NIR fluorescence label;
e) the NIR fluorescence signal of said second monoclonal antibody labeled with a NIR fluorescence label in said region of the solid tumor is measured and has decreased by at least 10%, preferably at least 20%, more preferably at least 30%, compared to the signal measured under b);
f) the patient receives a second dose with said non-labeled monoclonal antibody based on the result of the measurement of step e);
characterized in that the first and second antibody exhibit no cross reactivity.

Preferably the steps a) to f) are carried out as consecutive steps a), b), c), d), e) and f).

Another aspect of the invention is the use of a monoclonal antibody labeled with a NIR fluorescence label, specifically binding to a tumor antigen for the manufacture of a pharmaceutical composition for the treatment of a patient suffering from a solid tumor overexpressing said tumor antigen.

Another aspect of the invention is the use of a non-labeled, monoclonal antibody specifically binding to a tumor antigen for the manufacture of a medicament for the treatment of a solid tumor overexpressing said tumor antigen wherein a second monoclonal antibody labeled with a NIR fluorescence label, specifically binding to the same tumor antigen is used to determine the response to said treatment, characterized in that the first and second antibody exhibit no cross reactivity.

The term "to determine the response to said treatment" when used herein refers to the acquisition of the NIR fluorescence signals or images during the treatment of the patient suffering from a solid tumor overexpressing a tumor antigen with a non-labeled monoclonal antibody. E.g. several measurements in a region the solid tumor at different time points of the treatment can be performed. Or several NIR fluorescence images of the patient suffering from a solid tumor overexpressing a tumor antigen can be acquired. The "response" to the treatment can then be categorized for solid tumors overexpressing said tumor antigen in dependency of the decrease (increase) of the NIR fluorescence signal in said region of the solid tumor, which correlates to an decrease (increase) of the expression of tumor antigen in said region of the solid tumor (see e.g. Example 4, FIG. 4). In this connection another preferred aspect of the invention is the use of a non-labeled, monoclonal antibody specifically binding to a tumor antigen for the manufacture of a medicament for the treatment of a solid tumor wherein a second monoclonal antibody labeled with a NIR fluorescence label, specifically binding to the same tumor antigen is used to determine the expression of said tumor antigen, characterized in that the first and second antibody exhibit no cross reactivity.

Preferably the uses of a non-labeled monoclonal antibody specifically binding to a tumor antigen for the manufacture of a pharmaceutical composition as described above as well as the methods described below are characterized in that said tumor antigen, against which both monoclonal antibodies are specifically binding, is selected from the group consisting of EGFR, HER2/neu, HER3, HER4, Ep-CAM, CEA, TRAIL, TRAIL-receptor 1, TRAIL-receptor 2, lymphotoxin-beta receptor, CCR4, CD19, CD20, CD22, CD28, CD33, CD40, CD80, CSF-1R, CTLA-4, fibroblast activation protein (FAP), hepsin, melanoma-associated chondroitin sulfate proteoglycan (MCSP), prostate-specific membrane antigen (PSMA), VEGF receptor 1, VEGF receptor 2, IGF1-R, TSLP-R, TIE-1, TIE-2, TNF-alpha, TNF like weak inducer of apoptosis (TWEAK), IL-1R, preferably EGFR, HER2/neu, CEA, CD20, or IGF-1-R; more preferably HER2/neu.

Another aspect of the invention is a method for acquiring a NIR fluorescence image of a patient suffering from a solid tumor overexpressing a tumor antigen which has received a dose of a first, non-labeled, monoclonal antibody specifically binding to said tumor antigen and a dose of a second monoclonal antibody labeled with a NIR fluorescence label, specifically binding to the same tumor antigen, wherein the NIR fluorescence signal of in a region of the solid tumor is measured characterized in that the first and second antibody exhibit no cross reactivity.

Another aspect of the invention is a method for acquiring a NIR fluorescence image wherein the signal of a monoclonal antibody labeled with a NIR fluorescence label, specifically binding to a tumor antigen, in a region of a solid tumor is measured during the treatment of a patient suffering from a solid tumor overexpressing a tumor antigen with a monoclonal antibody specifically binding to the same tumor antigen, characterized in that the first and second antibody exhibit no cross reactivity.

Another aspect of the invention is a method for determining NIR fluorescence signal of a monoclonal antibody labeled with a NIR fluorescence label, specifically binding to a tumor antigen in a region of the solid tumor during the treatment of a patient suffering from a solid tumor overexpressing a tumor antigen with a non-labeled, monoclonal antibody specifically binding to the same tumor antigen, wherein the following steps are performed:

a) the patient receives a first dose with a second monoclonal antibody labeled with a NIR fluorescence label, specifically binding to the same tumor antigen, wherein the first and second antibody exhibit no cross reactivity, b) the NIR fluorescence signal of said second monoclonal antibody labeled with a NIR fluorescence label in a region of the solid tumor is measured, c) the patient receives a first dose with said non-labeled monoclonal antibody d) the patient receives a second dose with said second antibody labeled with a NIR fluorescence label, e) the NIR fluorescence signal of said second monoclonal antibody labeled with a NIR fluorescence label in said region of the solid tumor is measured and has decreased by at least 10%, preferably at least 20%, more preferably at least 30%, compared to the signal measured under b);

f) the patient receives a second dose with said non-labeled monoclonal antibody based on the result of the measurement of step e);

characterized in that the first and second antibody exhibit no cross reactivity.

Preferably the steps a) to f) are carried out as consecutive steps a), b), c), d), e) and f).

Preferably in such methods the signal/background ratio is at least 1.5, preferably 2.0.

Said "monoclonal antibody labeled with a NIR fluorescence label" is labeled with near infrared (NIR) fluorescence label suitable for acquiring of a NIR fluorescence image in the region of the solid tumor.

NIR fluorescence labels with excitation and emission wavelengths in the near infrared spectrum are used, i.e., 640-1300 nm preferably 640-1200 nm, and more preferably 640-900 nm. Use of this portion of the electromagnetic spectrum maximizes tissue penetration and minimizes absorption by physiologically abundant absorbers such as hemoglobin (<650 nm) and water (>1200 nm). Ideal near infrared fluorochromes for in vivo use exhibit:

(1) narrow spectral characteristics,
(2) high sensitivity (quantum yield),
(3) biocompatibility, and
(4) decoupled absorption and excitation spectra.

Various near infrared (NIR) fluorescence labels are commercially available and can be used to prepare probes according to this invention. Exemplary NIRF labels include the following: Cy5.5, Cy5 and Cy7 (Amersham, Arlington Hts., IL; IRD41 and IRD700 (LI-COR, Lincoln, Nebr.); NIR-1, (Dejindo, Kumamoto, Japan); LaJolla Blue (Diatron, Miami, Fla.); indocyanine green (ICG) and its analogs (Licha, K., et al., Proc. SPIE-Int. Soc. Opt. Eng. 2927 (1996) 192-198; Ito et al., U.S. Pat. No. 5,968,479); indotricarbocyanine (ITC; WO 98/47538); and chelated lanthanide compounds. Fluorescent lanthanide metals include europium and terbium. Fluorescence properties of lanthanides are described in Lackowicz, Principles of Fluorescence Spectroscopy 2nd Ed. Kluwar Academic New York (1999).

Accordingly, said "monoclonal antibody labeled with a NIR fluorescence label" is preferably labeled by a NIR fluorescence label selected from the group of Cy5.5, Cy5, Cy7, IRD41, IRD700, NIR-1, LaJolla Blue, indocyanine green (ICG), indotricarbocyanine (ITC) and SF64, 5-29, 5-36 and 5-41 (from WO 2006/072580), more preferably said antibody is labeled with a NIRF label selected from the group of Cy5.5, Cy5 and Cy7.

The methods used for coupling of the NIR fluorescence labels are well known in the art. The conjugation techniques of NIR fluorescence labels to an antibody have significantly matured during the past years and an excellent overview is given in Aslam, M., and Dent, A., Bioconjugation (1998) 216-363, London, and in the chapter "Macromolecule conjugation" in Tijssen, P., "Practice and theory of enzyme immunoassays" (1990), Elsevier, Amsterdam.

Appropriate coupling chemistries are known from the above cited literature (Aslam, supra). The NIR fluorescence label, depending on which coupling moiety is present, can be reacted directly with the antibody either in an aqueous or an organic medium. The coupling moiety is a reactive group or activated group which is used for chemically coupling of the fluorochrome label to the antibody. The fluorochrome label can be either directly attached to the antibody or connected to the antibody via a spacer to form a NIR fluorescence label conjugate comprising the antibody and a NIR fluorescence label. The spacer used may be chosen or designed so as to have a suitably long in vivo persistence (half-life) inherently.

"Measurement" or "determining" of the NIR fluorescence signal in a region the solid tumor is performed after administration of the labeled antibody to the patient. Or, if the composition according to the invention is used, after the administration of the composition of the non-labeled antibody and the labeled antibody to the patient. The measurement can be performed on defined time points after administration, e.g., 1 day, 2 days or 3 or even more days or any other time point appropriate for acquiring a comparable NIR fluorescence signal or image in a region the solid tumor. The duration of the measurement or the time point after administration can be adjusted by a person skilled in the art in a way to get an appropriate NIR fluorescence signal or image.

For the NIR fluorescence measurement different devices and techniques can be used, e.g. for external solid tumors like breast tumors, a SoftScan® apparatus from ART Advanced Research Technologies Inc. (http://www.art.ca/en/products/softscan.html) is suitable (Intes X, Acad. Radiol. 12 (2005) 934-947) For internal disease areas, like colorectal or lung cancer endoscopic techniques or a combination of microsurgery-endoscopy can be used.

An imaging system for NIR fluorescence measurement useful in the practice of this invention typically includes three basic components: (1) a near infrared light source, (2) a means for separating or distinguishing fluorescence emissions from light used for fluorochrome excitation, and (3) a detection system.

The light source provides monochromatic (or substantially monochromatic) near infrared light. The light source can be a suitably filtered white light, i.e., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas, D. A., et al., 1994, Proc. Natl. Acad. Sci. USA 91 4887-4891; Ntziachristos, V., et al., Proc. Natl. Acad. Sci. USA 97 2000 2767-2772; Alexander, W., 1991, J. Clin. Laser Med. Surg. 9 416-418.

A high pass filter (700 nm) can be used to separate fluorescence emissions from excitation light. A suitable high pass filter is commercially available from Omega optical.

In general, the light detection system can be viewed as including a light gathering/image forming component and a light detection/image recording component. Although the light detection system may be a single integrated device that incorporates both components, the light gathering/image forming component and light detection/image recording component will be discussed separately.

A particularly useful light gathering/image forming component is an endoscope. Endoscopic devices and techniques that have been used for in vivo optical imaging of numerous tissues and organs, including peritoneum (Gahlen, J., et al., J. Photochem. Photobiol. B 52 (1999) 131-135), ovarian cancer (Major, A. L., et al., Gynecol. Oncol. 66 (1997) 122-132), colon (Mycek, M. A., et al., Gastrointest. Endoscopy. 48 (1998) 390-394; Stepp, H., et al., Endoscopy 30 (1998) 379-386) bile ducts (Izuishi, K., et al., Hepatogastroenterology 46 (1999) 804-807), stomach (Abe, S., et al., Endoscopy 32 (2000) 281-286), bladder (Kriegmair, M., et al., Urol. Int. 63 (1999) 27-31; Riedl, C. R., et al., J. Endourol. 13 755-759), and brain (Ward, H. A., J. Laser Appl. 10 (1998) 224-228) can be employed in the practice of the present invention.

Other types of light gathering components useful in the invention are catheter-based devices, including fiber optics devices. Such devices are particularly suitable for intravascular imaging. See, e.g., Tearney, G. J., et al., Science 276 (1997) 2037-2039; Boppart, S. A., Proc. Natl. Acad. Sci. USA 94 (1997) 4256-4261.

Still other imaging technologies, including phased array technology (Boas, D. A., et al., Proc. Natl. Acad. Sci. 19 USA 91 (1994)4887-4891; Chance, B., Ann. NY Acad. Sci. 838 (1998) 29-45), diffuse optical tomography (Cheng, X., et al., Optics Express 3 (1998) 118-123; Siegel, A., et al., Optics Express 4 (1999) 287-298), intravital microscopy (Dellian, M., et al., Br. LT. Cancer 82 (2000) 1513-1518; Monsky, W. L., et al., Cancer Res. 59 (1999) 4129-4135; Fukumura, D., et al., Cell 94 (1998) 715-725), and confocal imaging (Korlach, J., et al., Proc. Natl. Acad. Sci. USA 96 (1999) 8461-8466; Rajadhyaksha, M., et al., J. Invest. Dermatol. 104 (1995)946-952; Gonzalez, S., et al., J. Med. 30 (1999) 337-356) can be employed in the practice of the present invention.

Any suitable light detection/image recording component, e.g., charge coupled device (CCD) systems or photographic film, can be used in the invention. The choice of light detection/image recording will depend on factors including type of light gathering/image forming component being used. Selecting suitable components, assembling them into a near infrared imaging system, and operating the system is within ordinary skill in the art.

Useful apparatuses for acquiring a NIR fluorescence image are e.g. the SoftScan® apparatus from ART Advanced Research Technologies Inc.; Image Station In-Vivo F; Image Station In-Vivo FX; In-Vivo Imaging System FX Pro from Molecular Imaging Systems, Carestream Health, Inc. (formerly Kodak Molecular Imaging Systems); Aerius™ Automated Infrared Imaging System and Odyssey Infrared Imaging System™ from LI-COR Biosciences; LB 983 NightOWL II from BERTHOLD TECHNOLOGIES or other appropriate devices.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 NIR fluorescence images of different solid tumors overexpressing and not overexpressing a HER2 tumor antigen:
In mice with
a) BT474 s.c (subcutaneous). model, a strongly HER2 overexpressing tumor model (3+ according to DAKO HercepTest®) (FIG. 1a),
b) a A549 s.c. model, a tumor model with no HER2 overexpression (0 according to DAKO HercepTest®) (FIG. 1b) and
c) in tumor free mice (FIG. 1c), pertuzumab labeled with Cy5 was injected i.v. at a single dose of 20 microgram per mouse and NIR fluorescence signal was measured after 24 h. Acquisition time was 2 seconds. The NIR fluorescence images indicate.

EXAMPLES

Introduction

Figure 1A:
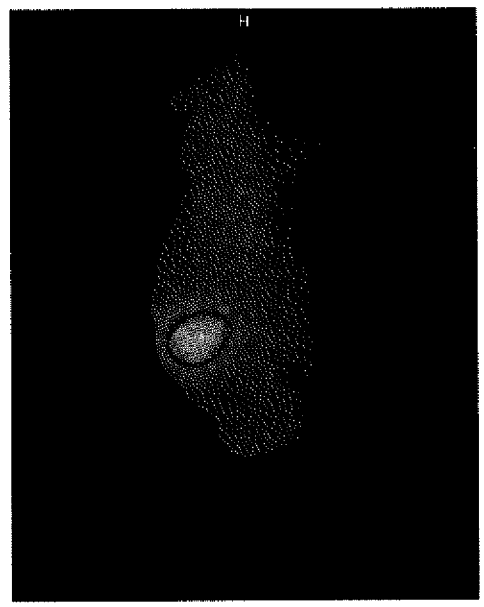
in FIG. 1a that i) the BT474 tumor cells overexpress HER2 tumor antigen and ii) a significant NIR fluorescence signal in the region of the solid tumor can be measured compared to the non-tumorous tissue.

The current study examined the NIR fluorescence imaging of monoclonal antibodies labeled with a NIR fluorescence label, specifically binding a tumor antigen alone or after or during a previous treatment with a non-labeled monoclonal antibody specifically binding to same tumor antigen (wherein the first and second antibody exhibit no cross reactivity) in different human xenograft models in which said tumor antigen was overexpressed or not overexpressed.

Cell Lines and Culture Conditions

The human breast cancer cell line KPL-4, kindly provided by J. Kureabashi, has been established from the malignant pleural effusion of a breast cancer patient with an inflammatory skin metastasis and overexpresses ErbB family receptors. (Kurebayashi, J., et al., Br. J. Cancer 79 (1999) 707-17) Tumor cells are routinely cultured in DMEM medium (PAA Laboratories, Austria) supplemented with 10% fetal bovine serum (PAA) and 2 mM L-glutamine (Gibco) at 37° C. in a water-saturated atmosphere at 5% $CO_2$. Culture passage is performed with trypsin/EDTA 1× (PAA) splitting twice/week. Cell passage P6 was used for the in vivo study.

The human breast cancer cell line BT474, which overexpresses Her2 was obtained from ATCC. The cells were grown in vitro in RPMI 1640 Medium containing 10% FBS (PAA), 2 mM L-Glutamine, 1 mM Na-Pyruvat and 10 mM Hepes at 37° C. in a water-saturated atmosphere at 5% $CO_2$. The cells of the third passage were used for subcutaneous injection into the mice.

The Her2 negative human A549 lung carcinoma cells were obtained from the DSMZ. The cells were routinely cultured using the same protocol as for the BT474 cell line, but without the addition of Hepes. Culture passage is performed with trypsin/EDTA 1× (PAA) splitting twice/week. Cell passage P3 was used for the in vivo study.

The EGF1R positive human Calu3 lung tumor cells were obtained from Roche, Kamakura. The cells were grown in vitro in Eagle's MEM with Earle's BSS, 10% FCS, 1 mM Na-pyruvat and 0.1 mM NEAA at 37° C. in a water-saturated atmosphere at 5% $CO_2$. The cells of the third passage were used for subcutaneous injection into the mice.

Animals

Female SCID beige (C.B.-17) mice and female Balb/c nude mice; age 10-12 weeks; body weight 18-20 g (Charles River, Sulzfeld, Germany) are maintained under specific-pathogen-free condition with daily cycles of 12 h light/12 h darkness according to international guidelines (GV-Solas; Felasa; TierschG). After arrival, animals are housed in the quarantine part of the animal facility for one week to get accustomed to new environment and for observation. Continuous health monitoring is carried out on regular basis. Diet food (Alltromin) and water (acidified pH 2.5-3) are provided ad libitum.

Tumor Cell Injection

Tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon 100 µm) the final cell titer was adjusted appropriately. Tumor cell suspension was carefully mixed with transfer pipette to avoid cell aggregation. Anesthesia was performed using a Stephens's inhalation unit for small animals with preincubation chamber (plexiglas), individual mouse nose-mask (silicon) and Isoflurane (Pharmacia-Upjohn, Germany) in a closed circulation system. Two days before injection the fur of the animals was shaved.

KPL-4 tumor cells (3×10e6 in 20 µl PBS) were injected orthotopically into the right penultimate inguinal mammary fat pad (i.m.f.p.) of each anesthetized mouse. For this orthotopic implantation, the cell suspension was injected through the skin under the nipple. Tumor cell injection corresponds to day 1 of the experiment.

BT474 tumor cells (5×10e6) were injected in 100 µl Matrigel (Becton Dickinson) subcutaneously into the right flank of the animals. 17 beta estradiol was supplemented via the drinking water. Initially, from day −1 until day 33 of the study the drinking water was supplemented with 2.5 µg 17 beta estradiol/ml water.

A549 tumor cells (1×10e7 in 100 µl PBS) were injected subcutaneously into the right flank of the animals.

Calu3 tumor cells (5×10e6 in 100 µl PBS) were injected subcutaneously into the right flank of the animals.

Monitoring of Clinical Symptoms and Body Weight

Animals were controlled daily for detection of clinical symptoms of adverse effects. For monitoring throughout the experiment, the body weight of the animals was documented two times weekly.

Acquisition of NIR Fluorescence Images

Non-invasive measurements or determination of NIR fluorescence signals can be accomplished by labeling monoclonal antibodies with appropriate NIR fluorescence labels. E.g. different monoclonal antibodies were labeled with a Cy5 or Cy5.5 or Cy7 dyes to monitor acquire NIR fluorescence images antibodies after i.v. injection into solid tumor carrying mice and for monitoring the development of said solid tumors and expression of tumor antigens originally overexpressed in said tumors during the treatment with non-labeled antibodies specifically binding to said tumor antigen. NIR fluorescence measurements were performed after application of antibodies at different time points thereafter using the BonSAI Imaging System from Siemens Medizintechnik, Germany. By summing up mean intensities of the pixels in the region of the solid tumor a NIR fluorescence signal can be determined which is specific for the solid tumor in dependency of e.g. the expression level of the tumor antigen, the antibody labeled with a certain NIR fluorescence image, the acquisition time, the time after application of the labeled antibody and the time after application of the non-labeled antibody intended for the treatment of said solid tumor, etc.

Results

Figure 1B:
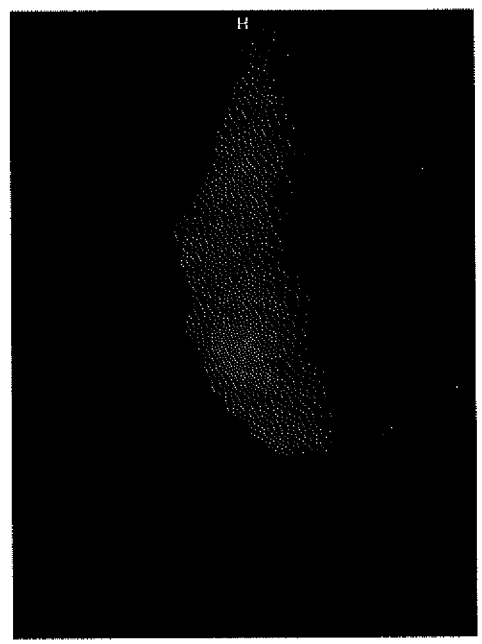
in FIG. 1b that i) the A549 tumor cells show no significant overexpression of the HER2 tumor antigen and ii) no significant NIR fluorescence signal in the region of the solid tumor can be detected compared to the non-tumorous tissue.
Figure 1C:
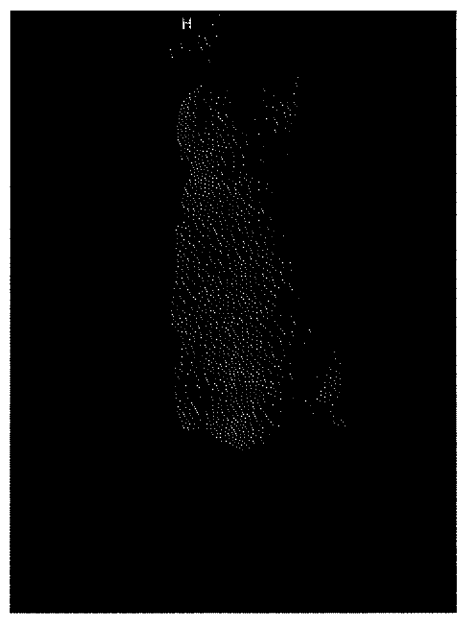
in FIG. 1c that i) the non-tumorous cells in the tumor-free mice show no significant overexpression of the HER2 tumor antigen and ii) no significant NIR fluorescence signal can be detected.

Example 1: NIR Fluorescence Imaging of Different Solid Tumors Overexpressing and not Overexpressing HER2 Tumor Antigen Female SCID beige mice carrying BT474 or A549 tumors were injected with i.v. with a single dose of 20 µg/mouse of pertuzumab at a time point when the tumor size was approximately 500 mm3. Tumor free SCID beige mice were also injected with the labeled monoclonal antibody and served as a control. One day thereafter NIR fluorescence signal was measured using the BONSAI system (Siemens Medizintechnik). Acquisition time was always 2 seconds. Results depicted in FIG. 1a indicate that the monoclonal antibody pertuzumab labeled with Cy5 allows the detection of Her2 overexpressing tumor cells BT474. In contrast, with A549 cells (FIG. 1b) which do not express the Her2 antigen, a NIR fluorescence signal was not detectable and also no NIR fluorescence signal could be generated in tumor free mice (FIG. 1c).

Figure 2A:
FIG. 2 NIR fluorescence images of solid tumors overexpressing HER2 tumor antigen:
In four mice with a KPL4 model, a strongly HER2 overexpressing tumor model (3+ according to DAKO HercepTest®), trastuzumab labeled with Cy5 (FIG. 2a) was injected i.v. in two mice, and pertuzumab labeled with Cy5 (FIG. 2b) was injected i.v. in the other two mice, all at a single dose of 50 microgram per mouse and NIR fluorescence signal was measured after 24 h. Acquisition time was 4 seconds. The NIR fluorescence images indicate that i) the KPL4 tumor cells overexpress HER2 tumor antigen and ii) a significant NIR fluorescence signal in the region of the solid tumor can be measured compared to the non-tumorous tissue using either trastuzumab labeled with Cy5 (FIG. 2a) or pertuzumab labeled with Cy5 (FIG. 2b).
Figure 2B:
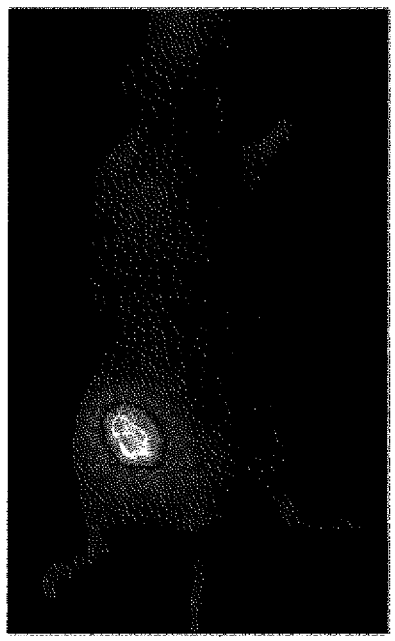

Example 2: NIR Fluorescence Imaging of Solid Tumors Overexpressing HER2 Tumor Antigen Female SCID beige mice carrying KPL-4 tumors were injected with Cy5 labeled trastuzumab (FIG. 2a) or Cy5 labeled pertuzumab (FIG. 2b). Labeled antibodies were injected i.v. with a dose of 50 µg/mouse. One day thereafter NIR fluorescence signal was measured with an acquisition time of 4 seconds. The results (FIG. 2) indicate that using Cy5 labeled trastuzumab (FIG. 2a) or Cy5 labeled pertuzumab (FIG. 2b) a comparable NIR fluorescence signal was detectable in the Her2 overexpressing cell line KPL-4.

Example 3

Figure 3A:
FIG. 3 NIR fluorescence images of solid tumors overexpressing HER2 tumor antigen during the treatment of a patient with non-labeled trastuzumab (early phase-48 h after first trastuzumab application)—use of pertuzumab labeled with Cy5 (no cross reactivity with trastuzumab) for NIR fluorescence imaging
In a KPL4 model, a strongly HER2 overexpressing tumor model (3+ according to DAKO HercepTest®), in a first administration non-labeled trastuzumab was injected i.p. at a single dose of 30 mg/kg, and 48 h later in a second administration either trastuzumab labeled with Cy5 (FIG. 3a) or pertuzumab labeled with Cy5 (FIG. 3b) was injected i.v. at a single dose of 50 microgram per mouse and NIR fluorescence signal was measured after 24 h after the second administration. Acquisition time was 4 seconds. The NIR fluorescence images indicate that i) during the treatment of a solid tumor overexpressing HER2 tumor antigen with trastuzumab (or a patient suffering from a solid tumor overexpressing HER2 tumor antigen), trastuzumab labeled with Cy5 (which is cross reactive with the non-labeled trastuzumab) is not suitable for the detection of a significant NIR fluorescence signal in the region of the solid tumor and (FIG. 3a); ii) during the treatment of a solid tumor overexpressing HER2 tumor antigen with trastuzumab, pertuzumab labeled with Cy5 (which exhibit no cross reactivity with non-labeled trastuzumab) is suitable for the detection of a significant NIR fluorescence signal in the region of the solid tumor (FIG. 3b)
Figure 3B:
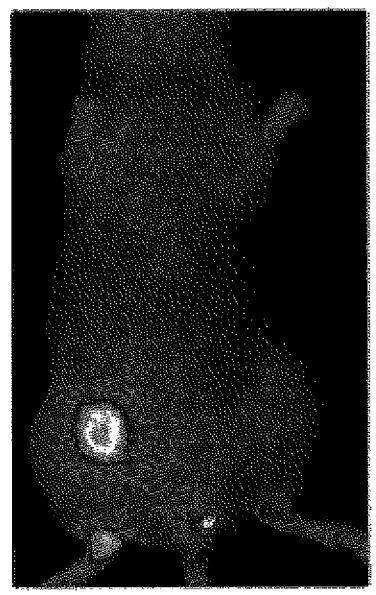

NIR Fluorescence Imaging of Solid Tumors Overexpressing HER2 Tumor Antigen During the Treatment of a Patient with Non-Labeled Trastuzumab (Early Phase-48 h after First Trastuzumab Application)—Use of Pertuzumab Labeled with Cy5 (No Cross Reactivity with Trastuzumab) for NIR Fluorescence Imaging Female SCID beige mice carrying KPL-4 tumors were injected i.p. with a single dose of 30 mg/kg trastuzumab. Two days thereafter one group of mice received Cy5 labeled trastuzumab (FIG. 3a) and mice of the second group were injected with Cy5 labeled pertuzumab (FIG. 3b). There was no significant difference in the tumor size in the two groups and the labeled antibodies were given i.v. at a dosage of 50 µg/mouse. NIR fluorescence signal was measured 24 hours thereafter with an acquisition time of 4 seconds. The background signal was 500 MFI (mean NIR fluorescence (NIRF) signal intensity [arbitrary units]) was measured with an acquisition time of 4 seconds. NIR fluorescence intensity was quantified by summing up the number and signal intensities of the pixels in the region of interest (ROI) or less were The results demonstrate that pre-injection with non-labeled trastuzumab prevents subsequent significant detection of Her2 expressing tumor cells when Cy5 labeled trastuzumab is applied as a signal of 530 MFI in the region of the tumor was measured, which is only little above the background signal of 500 MFI (FIG. 3a) Thus no significant NIR fluorescence signal can be detected after a previous treatment with trastuzumab, so that Cy5 labeled trastuzumab is not suitable for therapy monitoring during the treatment of a patient with trastuzumab. In contrast, application of Cy5 labeled pertuzumab (which binds to another epitope and is not crossreactive with trastuzumab) gave a signal of 1440 MFI in the region of the tumor (FIG. 3b). Thus a significant NIR fluorescence signal could be detected after a previous treatment with trastuzumab, so that Cy5 labeled pertuzumab is suitable for therapy monitoring during the treatment with trastuzumab, as it shows a clearly improved signal/background ratio of 2.88 (=1440MFI/500MFI Cy5 labeled pertuzumab after trastuzumab treatment) compared to the signal/background ratio of 1.06 (=530MFI/500MFI—Cy5 labeled trastuzumab after trastuzumab treatment). This allows a clearly better localization of the region of tumor than with the use of cross reactive antibodies; even when less NIRF labeled antibody is given. The results also clearly show that pertuzumab binds to an epitope which differs from the epitope recognized by trastuzumab, and thus that trastuzumab and pertuzumab exhibit no cross reactivity against the same HER2 tumor antigen (while trastuzumab and Cy5 labeled trastuzumab exhibit cross reactivity and no significant NIR fluorescence signal can be detected after a previous treatment with trastuzumab, so that Cy5 labeled trastuzumab is not suitable for therapy monitoring during the treatment with trastuzumab).

Example 4

Figure 4A:
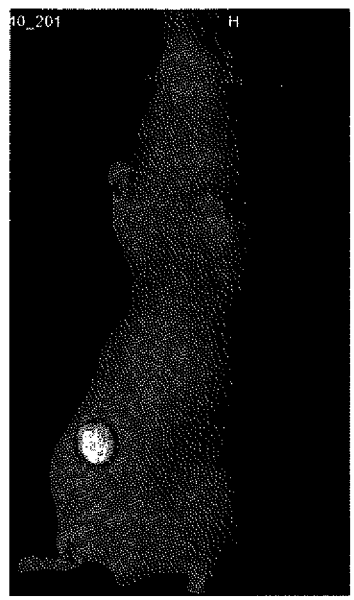
FIG. 4 NIR fluorescence images of solid tumors overexpressing HER2 tumor antigen during the weekly treatment with non-labeled pertuzumab (after second pertuzumab application)—use of trastuzumab labeled with Cy5 (no cross reactivity with pertuzumab) for NIR fluorescence imaging
In the KPL-4 model, pertuzumab was injected i.p. twice weekly. The first injection (loading dose) was 30 mg/kg and the second application (maintenance dose) was 15 mg/kg. Control animals received PBS. After 48 hours after the second administration mice of both groups were injected with trastuzumab labeled with Cy5 and 4 days later NIR fluorescence signal was measured using an acquisition time of 3 seconds. The NIR fluorescence images indicate that i) that that the NIR fluorescence signal in the pertuzumab treated mice (FIG. 4a) has decreased compared to the NIR fluorescence signal in the PBS treated mice (FIG. 4b), and ii) thus, at the solid HER2overexpressing KPL-4 tumor a response to the treatment with pertuzumab specifically binding to HER2 is detectable.
Figure 4B:

NIR Fluorescence Imaging of Solid Tumors Overexpressing HER2 Tumor Antigen During the Weekly Treatment with Non-Labeled Pertuzumab (48 h After Second Pertuzumab Application)—Use of Trastuzumab Labeled with Cy5 (No Cross Reactivity with Pertuzumab) for NIR Fluorescence Imaging Female SCID beige mice carrying KPL-4 tumors were treated with pertuzumab injected i.p. twice weekly. The first injection (loading dose) was 30 mg/kg and the second application (maintenance dose) was 15 mg/kg (FIG. 4a). Control animals received PBS only (FIG. 4b). After 48 hours mice of both groups were injected with 50 µg/mouse Cy5 labeled trastuzumab and 4 days later NIR fluorescence signal was measured using a acquisition time of 3 seconds. The figure FIG. 4a indicate that the NIRF signal in the pertuzumab treated mice is reduced compared to the NIR fluorescence signal in the PBS treated mice (FIG. 4b). Thus, at the solid HER2overexpressing KPL-4 tumor a response to the treatment with pertuzumab specifically binding to HER2 is detectable.

Example 5

Figure 5:
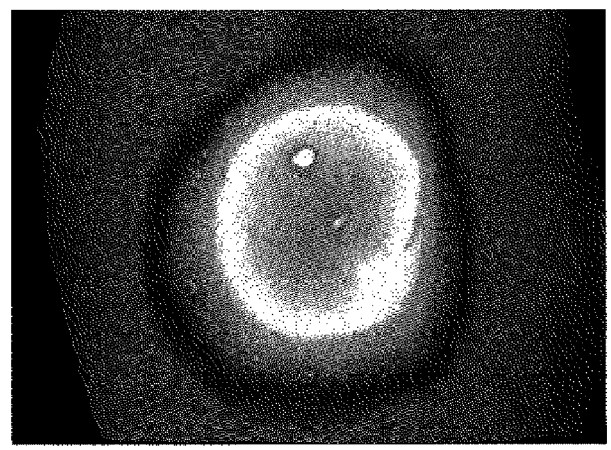
FIG. 5 NIR fluorescence imaging of solid tumors expressing EGFR tumor antigen during the treatment with non-labeled cetuximab—use of rhMab ICR62 labeled with Cy5 (no cross reactivity with cetuximab) for NIR fluorescence imaging
Female Balb/c nude mice carrying Calu3 tumors were injected i.p. with once weekly for four weeks at a dose of 2.5 mg/kg Cetuximab. Two days after the last treatment mice received 2 mg/kg Cy5 labeled rhMab ICR62. NIR fluorescence signal was measured 24 hours thereafter with an acquisition time of 4 seconds. The results demonstrate that pre-injection with non-labeled cetuximab allows subsequent detection of EGFR expressing tumor cells and exact localization of the tumor tissue when Cy5 labeled rhMab ICR62 is applied. This indicates that rhMab ICR62 binds to an epitope which differs from the epitope recognized by cetuximab, and shows that cetuximab and rhICR62 exhibit no cross reactivity against the same EGFR tumor antigen. Thus the NIR fluorescence image indicates that that at the solid EGFR expressing Calu3 tumor a response to the treatment with cetuximab specifically binding to HER2 is detectable with the non-crossreactive CY5 labeled rhMab ICR62.

NIR Fluorescence Imaging of Solid Tumors Expressing EGFR Tumor Antigen During the Treatment of a Patient with Non-Labeled Cetuximab—Use of rhMab ICR62 Labeled with Cy5 (No Cross Reactivity with Cetuximab) for NIR Fluorescence Imaging Female Balb/c nude mice carrying Calu3 tumors were injected i.p. with once weekly for five weeks at a dose of 2.5 mg/kg Cetuximab. Two days after the last treatment mice received 2 mg/kg Cy5 labeled rhMab ICR62 i.v. (FIG. 5). NIR fluorescence signal was measured 24 hours thereafter with an acquisition time of 4 seconds. The results demonstrate that pre-injection with non-labeled cetuximab allows subsequent detection of EGFR expressing tumor cells and exact localization of the tumor tissue when Cy5 labeled rhMab ICR62 is applied (FIG. 5). This indicates that rhMab ICR62 binds to an epitope which differs from the epitope recognized by cetuximab, and shows that cetuximab and rhICR62 exhibit no cross reactivity against the same EGFR tumor antigen.

The invention claimed is:
1. A method for near-infrared (NIR) fluorescence imaging of solid tumors in a patient during treatment with a first non-labeled monoclonal antibody, wherein the method comprises:
   a) administering to the patient a dose of the first non-labeled monoclonal antibody, wherein the first non-labeled monoclonal antibody specifically binds to a tumor antigen in the solid tumor;
   b) administering to the patient a dose of a second monoclonal antibody labeled with a NIR fluorescence label, wherein the second labeled monoclonal antibody also specifically binds to the tumor antigen, wherein the first and second monoclonal antibodies exhibit no cross reactivity; and
   c) measuring the NIR fluorescence signal of the second labeled monoclonal antibody in a region of the solid tumor.

2. The method of claim 1, wherein the signal/background ratio of the NIR fluorescence signal is at least 1.5.

3. The method of claim 1, wherein the first non-labeled monoclonal antibody is an anti-HER2 antibody.

4. The method of claim 3, wherein the first non-labeled monoclonal antibody is trastuzumab or pertuzumab.

5. The method of claim 1, wherein the first non-labeled monoclonal antibody is an anti-EGFR antibody.

6. The method of claim 5, wherein the first non-labeled monoclonal antibody is cetuximab or rhMab ICR62.

7. The method of claim 1, wherein the first non-labeled monoclonal antibody and the second labeled monoclonal antibody are co-administered to the patient during the treatment.

8. The method of claim 7, wherein the first non-labeled monoclonal antibody and the second labeled monoclonal antibody are co-administered simultaneously during the treatment.

9. The method of claim 7, wherein the first non-labeled monoclonal antibody and the second labeled monoclonal antibody are co-administered sequentially in either order during the treatment.

10. The method of claim 9, wherein the first non-labeled monoclonal antibody and the second labeled monoclonal antibody are co-administered in separate formulations.

11. A method for treating a patient suffering from a solid tumor overexpressing a tumor antigen, the method comprising:
   a) administering to the patient a first dose of a monoclonal antibody labeled with a near-infrared (NIR) fluorescence label, wherein the labeled monoclonal antibody specifically binds to the tumor antigen;
   b) measuring the NIR fluorescence signal in a region of the solid tumor, following the first dose of the labeled monoclonal antibody;
   c) administering to the patient a first dose of non-labeled monoclonal antibody, wherein the non-labeled monoclonal antibody also specifically binds to the tumor antigen, wherein the first and second monoclonal antibodies exhibit no cross reactivity;
   d) administering to the patient a second dose of the labeled monoclonal antibody labeled with a NIR fluorescence;
   e) measuring the NIR fluorescence signal in a region of the solid tumor, following the second dose of the labeled monoclonal antibody; and
   f) administering to the patient a second dose of the non-labeled monoclonal antibody, based on a decrease by at least 10% in the NIR fluorescence signal measured in step e) compared to the NIR fluorescence signal measured in step b).

12. The method of claim 11, wherein the administering in step f) is based on a decrease by at least 20% in the NIR fluorescence signal measured in step e) compared to the NIR fluorescence signal measured in step b).

13. The method of claim 11, wherein the administering in step f) is based on a decrease by at least 30% in the NIR fluorescence signal measured in step e) compared to the NIR fluorescence signal measured in step b).

14. The method of claim 11, wherein the non-labeled monoclonal antibody is an anti-HER2 antibody.

15. The method of claim 14, wherein the non-labeled monoclonal antibody is trastuzumab or pertuzumab.

16. The method of claim 11, wherein the non-labeled monoclonal antibody is an anti-EGFR antibody.

17. The method of claim 16, wherein the non-labeled monoclonal antibody is cetuximab or rhMab ICR62.

18. A method for near-infrared (NIR) fluorescence imaging of solid tumors in a patient during treatment with a first non-labeled monoclonal antibody, wherein the method comprises:
   a) co-administering to the patient in a single formulation a dose of the first non-labeled monoclonal antibody and a second monoclonal antibody labeled with a NIR fluorescence label, wherein the first non-labeled monoclonal antibody specifically binds to a tumor antigen in the solid tumor and the second labeled monoclonal antibody also specifically binds to the tumor antigen, wherein the first and second monoclonal antibodies exhibit no cross reactivity; and
   b) measuring the NIR fluorescence signal of the second labeled monoclonal antibody in a region of the solid tumor.

19. The method of claim 18, wherein the signal/background ratio of the NIR fluorescence signal is at least 1.5.

20. The method of claim 18, wherein the first non-labeled monoclonal antibody is an anti-HER2 antibody.

21. The method of claim 20, wherein the first non-labeled monoclonal antibody is trastuzumab or pertuzumab.

22. The method of claim 18, wherein the first non-labeled monoclonal antibody is an anti-EGFR antibody.

23. The method of claim 22, wherein the first non-labeled monoclonal antibody is cetuximab or rhMab ICR62.

* * * * *